| United States Patent [19] | [11] Patent Number: 4,752,620 |
| Roberts | [45] Date of Patent: Jun. 21, 1988 |

[54] METHOD OF TREATING PAIN WITH UREA AND GLYOXAL COMPOSITIONS

[76] Inventor: David Roberts, 7241 Mission Hills Dr., Las Vegas, Nev. 89113

[21] Appl. No.: 934,243

[22] Filed: Nov. 21, 1986

[51] Int. Cl.$^4$ .................... A61U 31/11; A61U 31/17
[52] U.S. Cl. .................................... 514/588; 514/693
[58] Field of Search ............................. 514/588, 693

[56] References Cited

U.S. PATENT DOCUMENTS

| 3,650,280 | 3/1972 | Roberts et al. | 137/7 |
| 3,679,792 | 7/1972 | Litchfield et al. | 424/48 |
| 3,983,252 | 9/1976 | Buchalter | 424/333 |
| 4,048,299 | 9/1977 | Litchfield et al. | 424/49 |
| 4,122,192 | 10/1978 | Fellows | 424/333 |

OTHER PUBLICATIONS

Merck Index; 9th Ed. 1976. pp. 584–585.

*Primary Examiner*—Stanley J. Friedman
*Attorney, Agent, or Firm*—Morgan & Finnegan

[57] ABSTRACT

A method of alleviating or "breaking" pain caused by contusions to the skin using a composition containing glyoxal, urea and an inert carrier.

6 Claims, No Drawings

METHOD OF TREATING PAIN WITH UREA AND GLYOXAL COMPOSITIONS

This invention relates to the use of a topical composition for the alleviation of pain. More particularly, it contemplates the use of urea and glyoxal compositions for topical application to body contusions, e.g., bruises, scrapes, burns and cuts, to relieve pain.

BACKGROUND OF THE INVENTION

Urea and glyoxal compositions for use in the cosmetic treatment of hair were described in U.S. Pat. No. 3,650,280. These compositions aided in beautifying hair.

Glyoxal-containing compositions have been used for such purposes as disinfection (U.S. Pat. No. 3,983,252 and U.S. Pat. No. 4,122,192), and anti-cavity activity (U.S. Pat. No. 4,048,290 and U.S. Pat. No. 3,679,792). However, glyoxal-containing compositions have not been recognized as being useful for alleviating pain from a contusion, bruise, minor scrape, cut or burn.

The inventor has found that glyoxal-containing formulas may be used as topical analgesics to alleviate skin pain caused by contusions such as bruises, minor scrapes, burns and cuts.

It is, therefore, an object of this invention to provide a method for alleviating body pain caused by body contusions, such as muscle pain, scrapes, burns, cuts and bruises.

Yet another object of this invention is to provide a method of "breaking" pain by application of a topical analgesic composition.

It is another object of this invention to provide a method of using urea and glyoxal compositions as analgesics.

It is another object of this invention to provide a method of treating topical skin pain using urea and glyoxal compositions which are non-toxic.

Another object of this invention is to provide a method of soothing pain using a topical analgesic composition.

DESCRIPTION OF THE INVENTION

Surprisingly, the compositions set forth in U.S. Pat. No. 3,650,280 which were previously thought only to benefit the hair and used only for that purpose, can be used in the method of this invention to provide analgesic activity to the skin.

When applied to the desired damaged area of the body, such as a bruise, cut, burn or scrape, a quantity of a composition which contains:
a. glyoxal;
b. urea; and
c. an inert pharmacological carrier Will provide analgesic action to the area to which it is applied by stopping, or "breaking", the pain associated with the contusion or damaged skin.

A preferred composition will contain:
a. from about 0.08 to about 4 percent by weight of glyoxal;
b. from about 0.2 to about 9 percent by weight of urea; and
c. as an inert carrier, water, a lower alkanol, or a mixture of water and a lower alkanol Another preferred composition will also contain a minor proportion of benzyl alcohol.

Still another preferred composition will contain a minor proportion of diethylene glycol monoethyl ether.

Especially preferred compositions will contain minor proportions of both benzyl alcohol and diethylene glycol monoethyl ether.

Such compositions will preferably contain:
d. from about 0.1 to about 4 percent by weight of benzyl alcohol; and
e. from about 0.1 to about 4 percent by weight of diethylene glycol monoethyl ether.

Preferred compositions are those wherein the pH is from about 4 to about 6. Excluded, of course, are media too acidic to be employed on the skin without imparting damage.

The urea and glyoxal ingredients useful in the compositions used in the method of this invention are items of commerce. Preferably, the glyoxal ingredient is used in the method of this invention in its "unpurified" form, as obtained from American Hoechst Company. Glyoxal is an essential element of the composition useful in the method of this invention, although its contribution to the analgesic action of the composition is not well understood. It is believed that the composition somehow "breaks" the pain, or stops the message of pain from travelling to the brain. The compositions of this invention may break the pain of body contusions, bruises, scrapes, burns and cuts as well as arthritis.

Suitable carriers comprise a class of nonirritating liquids which may be safely applied to the skin of mammals, such as water, alcohols, especially lower alcohols of from two to six carbon atoms, e.g., ethanol, isopropanol, etc., mixtures of water and lower alcohols, fats, such as lanolin and the like.

Suitable formulations depending on the end use contemplated can be prepared easily by those skilled in the art. Generally, for economic reasons, and for ease of application, the composition will contain a minor proportion, i.e., less than 50 percent by weight of urea, and glyoxal, and major proportion of carrier. For most purposes, the ratio of glyoxal to urea will not be critical, the advantages being secured at ratios ranging from about 1:10 to about 10:1 by weight of each. Most preferably the best properties will be obtained with compositions containing from about 0.04 to about 8 percent urea and preferably from about 0.08 to about 4 percent by weight of glyoxal and from about 0.1 to about the solubility limit in water, but preferably from about 0.20 to about 9 percent of urea.

If either benzyl alcohol, or diethylene glycol monoethyl ether, or both is added to basic formulation, in minor proportions, e.g., either or both together providing less than 50 percent by weight of final composition, there is preferred enhancement in properties of the instant compositions. Compositions containing either of these ingredients or, preferably both of them, are important embodiments hereof.

The compositions of this invention should have bactericidal action as well as cidal action against molds. The compositions of this invention should be non-toxic.

Of course, as will be obvious to those skilled in the art, a variety of conventional additives may be used in the instant compositions to secure additional objectives. For example, small amounts of stabilizers and sequestrants, e.g. sorbic acid or its salts; gelling agents, such as polyethers, opacifiers; hydrolized proteins, perfumes and the like, may be used.

Those skilled in art of formulating topical compositions will be well aware of the manipulative techniques needed to provide the compositions in the form of solutions, dispersions, lotions, gels, creams and the like.

Preferred formulations will be exemplified in detail hereinafter. In one method, the liquid ingredients are blended, then the solids are mixed in. In another method powdered solids, e.g., urea and solid additives are mixed together first, then blended with part of the inert pharmacological carrier, then the liquid components, e.g., glyoxal, and benzyl alcohol and diethylene glycol monoethyl ether, if used, and opacifier, and other liquid additives, if desired, are blended with the reserved part of the pharmacological carrier, then final blending is made. If necessary, the pH is adjusted to the desired level by adding the required amount of acid, e.g., hydrochloric acid, or alkali, e.g., sodium hydroxide solution. Sodium hydroxide solution may also be used to alter the viscosity to the desirable consistency increasing the concentration of sodium hydroxide will increase the viscosity of the composition. Likewise, decreasing the sodium hydroxide level will decrease the viscosity.

DESCRIPTION OF THE PREFERRED EMBODIMENTS

The following examples describe the preparation of compositions for use in the method according to the present invention.

EXAMPLE 1

A composition having the following formulations, expressed as parts by weight, is prepared:
glyoxal: 1.4
urea: 4
water 94.6

The urea is mixed with the water until dissolved. Then glyoxal is added as a 40 percent aqueous solution. Finally, the mixture is blended until uniform and the pH is adjusted to 4 to 6, if necessary, with acid or alkali.

A quantity of the composition is applied to a confused, bruised or scraped area of the skin in a layer of about 2 mm thickness. Almost instantaneously, the area feels soothed and the pain is alleviated.

EXAMPLE 2

Compositions having the following formulations, expressed as parts by weight, are prepared:

| Glyoxal | 1.4 | 1.4 | 1.4 | 1.4 | 1.2 | 1.6 |
|---|---|---|---|---|---|---|
| Urea | 4 | 4 | 4 | 4 | 4 | 4 |
| Benzyl alcohol | | 2 | | 2 | 2 | 2 |
| Diethylene glycol monoethyl ether | | | 2 | 2 | 2 | 2 |
| Water (distilled) | | 92.6 | 92.6 | 90.6 | 90.8 | 90.4 |
| Isopropanol | 94.6 | | | | | |

The pH is adjusted to 4 to 6, if necessary by adding 0.2N HCl or 0.5N NaOH.

The compositions are applied liberally to the skin where it has been contused, scraped and burned. Instantaneously the skin feels less painful and relieved.

EXAMPLE 3

A composition having the following formulation, expressed as parts by weight, is prepared.

| glyoxal | 0.4 |
|---|---|
| urea | 2.0 |
| hydrolyzed protein (Wilson, X-1000) | 0.1 |
| Carboxypolymethylene (Union Carbide Carbopol 940) | 1.0 |
| sodium hydroxide | 0.175 |
| diethyleneglycol monoethyl ether (Union Carbide, Carbitol) | 2.0 |
| benzyl alcohol | 2.0 |
| potassium sorbate | 0.05 |
| formalin | 0.25 |
| perfume | q.s |
| opacifier | q.s. |
| water q.s | 100.00 |

The composition is applied to an arthritic area according to the method of this invention. The arthritic area of the skin is relieved of pain.

EXAMPLE 4

Compositions having the following formulation, expressed as parts by weight, are prepared:

| glyoxal | 0.33–1.2 |
|---|---|
| urea | 1–4 |
| hydrolyzed protein (Wilson, X-1000) | 0.25 |
| polyvinylpyrrolidone (PVP NPK 30) | 0.05 |
| diethylenglycol mono ethyl ether (Union Carbide, Carbitol) | 1–2 |
| benzyl alcohol | 1–2 |
| Carboxypolymethylene (Union Carbide Carbopol 940) | 0.8–1.0 |
| sodium hydroxide | 0.15–0.2 |
| formalin | 0.25 |
| perfume | q.s |
| opacifier | q.s |
| water q.s | 100.00 |

This composition is applied to a painful or chafed area of the skin according to the method of this invention.

Although specific embodiments of the invention have been described herein, it is obvious that many variations will suggest themselves to those skilled in the art after reading this detailed description. It is intended to include all obvious variations and modifications within the spirit and scope of the appended claims.

What is claimed is:

1. A method for relieving pain, in a mammal, from body contusions which comprises topically applying to the skin of said mammal, an effective amount of an analgesic composition comprising:
   a. from about 0.08 to about 4 percent by weight of glyoxal;
   b. from about 0.04 to about 8 percent by weight of urea; and
   c. as an inert carrier, water, a lower alkanol, or a mixture of water and lower alkanol, whereby said skin is substantially instaneously relieved of pain.

2. A method according to claim 1 wherein said composition also includes from about 0.1 to about 4 percent of benzyl alcohol.

3. A method according to claim 1 wherein said composition also includes from about 0.1 to about 4 percent of diethylene glycol monoethyl ether.

4. A method according to claim 1 wherein said composition also includes:

d. from about 0.1 to about 4 percent by weight of benzyl alcohol; and e. from about 0.1 to about 4 percent by weight of diethylene glycol monoethyl ether.

5. A method for relieving pain, in a mammal, from body contusions which comprises topically applying to the skin of said mammal, an effective amount of an analgesic composition comprising (a) an analgesic effective amount of glycoxal, (b) an analgesic effective amount of urea; and (c) an inert carrier selectd from the group consisting of water, a lower alkanol and mixtures thereof.

6. A method of relieving pain from body contusions comprising applying to the skin of a composition as defined in claim 4.

* * * * *